(12) United States Patent
Diehl et al.

(10) Patent No.: US 8,138,212 B2
(45) Date of Patent: Mar. 20, 2012

(54) SYNERGISTIC MICROBICIDAL COMPOSITIONS

(75) Inventors: Megan Anne Diehl, Line Lexington, PA (US); Dolores Ann Shaw, Collegeville, PA (US)

(73) Assignee: Rohm and Haas Company, Philadelphia, PA (US)

(*) Notice: Subject to any disclaimer, the term of this patent is extended or adjusted under 35 U.S.C. 154(b) by 73 days.

(21) Appl. No.: 12/842,122

(22) Filed: Jul. 23, 2010

(65) Prior Publication Data
US 2011/0028525 A1 Feb. 3, 2011

Related U.S. Application Data

(60) Provisional application No. 61/273,049, filed on Jul. 30, 2009.

(51) Int. Cl.
*A01N 43/80* (2006.01)
*A01N 1/00* (2006.01)
*A01N 3/00* (2006.01)

(52) U.S. Cl. ........................ 514/372; 514/373

(58) Field of Classification Search .............. 514/372, 514/373
See application file for complete search history.

(56) References Cited

U.S. PATENT DOCUMENTS

| 5,160,666 A | 11/1992 | Lindner et al. |
|---|---|---|
| 5,489,588 A | 2/1996 | Hsu et al. |
| 6,159,999 A | 12/2000 | Yagi et al. |
| 6,511,673 B1 | 1/2003 | Chia et al. |
| 2006/0106024 A1 | 5/2006 | Levy et al. |
| 2007/0078118 A1 | 4/2007 | Levy et al. |
| 2009/0143341 A1 | 6/2009 | Wingenfeld et al. |
| 2009/0156570 A1 | 6/2009 | Antoni-Zimmermann et al. |
| 2009/0163445 A1 | 6/2009 | Diehl et al. |

FOREIGN PATENT DOCUMENTS

| DE | 19548710 | 6/1997 |
|---|---|---|
| EP | 1332675 | 8/2003 |
| WO | 03/013491 | 2/2003 |
| WO | 2007007080 | 1/2007 |

OTHER PUBLICATIONS

Techical Data Sheet for Microcare MTD1; THOR GmbH.

*Primary Examiner* — Raymond Henley, III
(74) *Attorney, Agent, or Firm* — Thomas D. Rogerson

(57) ABSTRACT

This invention relates to synergistic combinations of selected isothiazolin-3-one microbicides in combination with a second microbicide or formulation ingredient or raw material. The combinations have greater efficacy than would be expected from combinations of the individual components. The combinations include mixtures of (a) Methyl-4-isothiazolin-3-one or (b) 1,2-Benzisothiazolin-3-one with one or more of a variety of other compounds.

2 Claims, No Drawings

SYNERGISTIC MICROBICIDAL COMPOSITIONS

This application claims the benefit of priority under 35 U.S.C. §119(e) of U.S. Provisional Patent Application No. 61/273,049 filed on Jul. 30, 2009.

This invention relates to synergistic combinations of selected microbicides with other microbicides, formulation ingredients, or raw materials that result in a composition with surprisingly greater antimicrobial activity than one would expect from combinations of the individual components, based on their individual antimicrobial activity.

In some cases, commercial microbicides cannot provide effective control of certain microorganisms, even at high use concentrations, due to weak activity against certain types or species of microorganisms and/or due to aggressive environmental conditions. Combinations of different microbicides are sometimes used to provide overall control of multiple species of microorganisms in a particular end use environment. For example, combinations of 2-methyl-4-isothiazolin-3-one with other biocides are disclosed in U.S. Pat. App. Pub. No. 2004/0014799 and combinations of 1,2-benzisothiazolin-3-one with other biocides are disclosed in U.S. Pat. App. Publ No. 2006/0106024. However, there is still a need for additional combinations of microbicides, or combinations of microbicides with formulation ingredients or raw materials, having enhanced activity against various strains of microorganisms to provide for their effective control. In addition, there is still a need for combinations containing lower levels of individual microbicides for environmental and economic benefit. The problem addressed by this invention is to provide such additional combinations of isothiazolin-3-one microbicides with other microbicides, formulation ingredients, or raw materials.

A first embodiment of the present invention is directed to a composition comprising a microbicidally synergistic mixture of:
(a) 2-methyl-4-isothiazolin-3-one; and
(b) one or more compounds selected from the group consisting of anisic acid, decylene glycol, diethylene triamine pentacetic acid (DTPA), hydroxyethyl ethylenediamine triacetic acid (HEDTA), imminodisuccinate (IDS), maleic acid, methyl glycine diacetic acid (MDGA), phenoxypropanol, phytic acid, and propionic acid.

A second embodiment of the present invention is directed to a composition comprising a microbicidally synergistic mixture of:
(a) 1,2-benzisothiazolin-3-one; and
(b) one or more compounds selected from the group consisting of anisic acid, capric acid, decylene glycol, diethylene triamine pentacetic acid (DTPA), etidronic acid, gluconic acid, hydroxyethyl ethylenediamine triacetic acid (HEDTA), imminodisuccinate (IDS), maleic acid, methyl glycine diacetic acid (MDGA), phenoxypropanol, phytic acid, and propionic acid.

"MIT" is 2-methyl-4-isothiazolin-3-one, also referred to by the name 2-methyl-3-isothiazolone or methylisothiazolinone. "BIT" is 1,2-benzisothiazolin-3-one. "Anisic acid" is 4-methoxybenzoic acid. "Capric Acid" is decanoic acid. "Ddecylene glycol" is 1,2-decanediol. "DTPA" is diethylene triamine pentacetic acid. "Etidronic acid" is hydroxyethylidene bisphosphoric acid. "Gluconic acid" is pentahydroxyhexanoic acid. "HEDTA" is hydroxyethyl ethylenediamine triacetic acid. "IDS" is iminodisuccinate. "Maleic acid" is 2-butenedioic acid. "MDGA" is methyl glycine diacetic acid. "Phenoxypropanol" is propylene glycol phenyl ether. "Phytic acid" is inositol hexaphosphoric acid. "Propionic acid" is ethanecarboxylic acid.

As used herein, the following terms have the designated definitions, unless the context clearly indicates otherwise. The term "microbicide", "biocide", "preservative" or "antimicrobial" refers to a compound capable of killing, inhibiting the growth of, or controlling the growth of microorganisms at a locus; microbicides include, but are not limited to, bactericides, fungicides and algicides. The term "microorganism" includes, for example, fungi (such as, for example, yeast and mold), bacteria, and algae. The term "locus" refers to an industrial system or product, a personal care system or product, a home care system or product, or other environment subject to contamination by microorganisms. The term "compound" refers to a microbicide, a formulation ingredient, or a raw material. The following abbreviations are used throughout this specification: ppm=parts per million by weight (weight/weight), mL=milliliter, ATCC=American Type Culture Collection, MBC=minimum biocidal concentration, and MIC=minimum inhibitory concentration. Unless otherwise specified, temperatures are in degrees Celcius (° C.), and references to percentages (%) are by weight. Amounts of organic microbicides are given on an active ingredient basis in ppm (w/w). Ratios are by weight and may be expressed as, for example, 1/400 or 1:400.

The compositions of the present invention have been found to provide unexpectedly enhanced microbicidal efficacy at an active ingredient level lower than what would be expected for a combination of the individual microbicides, or the microbicides in combination with formulation ingredients or raw materials, based on their individual efficacy.

In one embodiment of the invention, the composition comprises MIT and anisic acid. In another embodiment, the weight ratio of MIT to anisic acid is from 1/5 to 1/13.

In one embodiment of the invention, the composition comprises MIT and decylene glycol. In another embodiment, the weight ratio of MIT to decylene glycol is from 1/0.8 to 1/50.

In one embodiment of the invention, the composition comprises MIT and DTPA. In another embodiment, the weight ratio of MIT to DTPA is from 1/0.05 to 1/20.

In one embodiment of the invention, the composition comprises MIT and HEDTA. In another embodiment, the weight ratio of MIT to HEDTA is from 1/0.05 to 1/160.

In one embodiment of the invention, the composition comprises MIT and IDS. In another embodiment, the weight ratio of MIT to IDS is from 1/2 to 1/300.

In one embodiment of the invention, the composition comprises MIT and maleic acid. In another embodiment, the weight ratio of MIT to maleic acid is from 1/50 to 1/300.

In one embodiment of the invention, the composition comprises MIT and MDGA. In another embodiment, the weight ratio of MIT to MDGA is from 1/15 to 1/250.

In one embodiment of the invention, the composition comprises MIT and phenoxypropanol. In another embodiment, the weight ratio of MIT to phenoxypropanol is from 1/4 to 1/200.

In one embodiment of the invention, the composition comprises MIT and phytic acid. In another embodiment, the weight ratio of MIT to phytic acid is from 1/10 to 1/100.

In one embodiment of the invention, the composition comprises MIT and propionic acid. In another embodiment, the weight ratio of MIT to propionic acid is from 1/7.5 to 1/25.

In one embodiment of the invention, the composition comprises BIT and anisic acid. In another embodiment, the weight ratio of BIT to anisic acid is from 1/30 to 1/1000.

In one embodiment of the invention, the composition comprises BIT and capric acid. In another embodiment, the weight ratio of BIT to capric acid is from 1/30 to 1/600.

In one embodiment of the invention, the composition comprises BIT and decylene glycol. In another embodiment, the weight ratio of BIT to decylene glycol is from 1/50 to 1/133.

In one embodiment of the invention, the composition comprises BIT and DTPA. In another embodiment, the weight ratio of BIT to DTPA is from 1/0.7 to 1/100.

In one embodiment of the invention, the composition comprises BIT and etidronic acid. In another embodiment, the weight ratio of BIT to etidronic acid is from 1/27 to 1/200.

In one embodiment of the invention, the composition comprises BIT and gluconic acid. In another embodiment, the weight ratio of BIT to gluconic acid is from 1/80 to 1/600.

In one embodiment of the invention, the composition comprises BIT and HEDTA. In another embodiment, the weight ratio of BIT to HEDTA is from 1/13 to 1/1200.

In one embodiment of the invention, the composition comprises BIT and IDS. In another embodiment, the weight ratio of BIT to IDS is from 1/800 to 1/1300.

In one embodiment of the invention, the composition comprises BIT and maleic acid. In another embodiment, the weight ratio of BIT to maleic acid is from 1/30 to 1/1000.

In one embodiment of the invention, the composition comprises BIT and MDGA. In another embodiment, the weight ratio of BIT to MDGA is from 1/20 to 1/1600.

In one embodiment of the invention, the composition comprises BIT and phenoxypropanol. In another embodiment, the weight ratio of BIT to phenoxypropanol is from 1/20 to 1/1600.

In one embodiment of the invention, the composition comprises BIT and phytic acid. In another embodiment, the weight ratio of BIT to phytic acid is from 1/6 to 1/300.

In one embodiment of the invention, the composition comprises BIT and propionic acid. In another embodiment, the weight ratio of BIT to propionic acid is from 1/2 to 1/1000.

The microbicides, formulation ingredients, and raw materials in each composition of this invention may be used "as is" or may first be formulated with a solvent or a solid carrier. Suitable solvents include, for example, water; glycols, such as, for example, ethylene glycol, propylene glycol, diethylene glycol, dipropylene glycol, polyethylene glycol, and polypropylene glycol; glycol ethers; alcohols, such as, for example, methanol, ethanol, propanol, and phenethyl alcohol; ketones, such as, for example, acetone and methyl ethyl ketone; esters, such as, for example, ethyl acetate, butyl acetate, triacetyl citrate, and glycerol triacetate; carbonates, such as, for example, propylene carbonate and dimethyl carbonate; and mixtures thereof. In some embodiments the solvent is selected from water, glycols, glycol ethers, esters, and mixtures thereof. Suitable solid carriers include, for example, cyclodextrins, silicas, diatomaceous earth, clays, inorganic salts, sugars, starches, polymerics, silicates, clathrates, zeolites, waxes, cellulosic materials, (including, for example, chloride, nitrate, bromide, and sulfate derivatives), and charcoal.

When a microbicide, formulation ingredient, or raw material component is formulated in a solvent, the formulation may optionally contain surfactants. Surfactants include, for example, anionic, nonionic, cationic, amphoteric surfactants and mixtures thereof. When such formulations contain surfactants, they are generally in the form of emulsion concentrates, emulsions, microemulsion concentrates, or microemulsions. Emulsion concentrates form emulsions upon the addition of a sufficient amount of water. Microemulsion concentrates form microemulsions upon the addition of a sufficient amount of water. Such emulsion and microemulsion concentrates are generally well known in the art. U.S. Pat. No. 5,444,078 may be consulted for further general and specific details on the preparation of various microemulsions and microemulsion concentrates. In some embodiments, such emulsions and microemulsions are free of surfactants.

A microbicide, formulation ingredient, or raw material component also may be formulated in the form of a dispersion. The solvent component of the dispersion may be, for example, an organic solvent or water. In some embodiments the solvent component is water only. Dispersions may contain one or more optional adjuvants such as, for example, co-solvents, thickeners, anti-freeze agents, dispersants, fillers, pigments, surfactants, biodispersants, sulfosuccinates, terpenes, furanones, polycations, stabilizers, scale inhibitors, and anti-corrosion additives.

When the microbicide, formulation ingredient, or raw material are each first formulated with a solvent, the solvent used for the first component may be the same as or different from the solvent used to formulate the other component. In some embodiments water is preferred for many biocide applications. In some embodiments the two solvents are miscible.

Those skilled in the art will recognize that the microbicide, formulation ingredient, or raw material components of the present invention may be added to a locus sequentially, simultaneously, or may be combined before being added to the locus. In one embodiment of the invention, the first component and the second component are added to a locus simultaneously or sequentially. When the components are added simultaneously or sequentially, each may independently contain one or more optional adjuvants.

The compositions of the present invention can be used to prevent or inhibit the growth of microorganisms or higher forms of aquatic life (such as, for example, protozoans, invertebrates, bryozoans, dinoflagellates, crustaceans, mollusks, etc) by introducing a microbicidally effective amount of the compositions onto, into, or at a locus subject to microbial attack. Suitable loci include, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household and personal care products, such as, for example, bathroom and kitchen cleaners; cosmetics; lotions, moisturizers, toiletries; hair styling creams, pastes, or gums; conditioners, 2 in 1 conditioning shampoos, body wash/shower gels, liquid soaps, sunscreen lotions and sprays, tanning lotions, skin care lotions, one and two-part hair dyes, permanent waving formulations, soaps; detergents; cleaners; floor polishes; laundry rinse water; metalworking fluids; conveyor lubricants; hydraulic fluids; leather and leather products; textiles; textile products; wood and wood products, such as, for example, plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

In one embodiment, the compositions of the present invention are used to inhibit the growth of microorganisms at a locus selected from one or more of cosmetics; sunscreens, lotions, toiletries; hair styling creams, pastes, or gums; conditioners, 2 in 1 conditioning shampoos, body wash/shower gels, liquid soaps, sunscreen lotions and sprays, tanning lotions, skin care lotions, one and two-part hair dyes, permanent waving formulations, soaps; and detergents.

One skilled in the art will recognize that the specific amount of a composition of this invention necessary to inhibit or control the growth of microorganisms and higher aquatic life forms in a locus depends upon the type, species, and/or identity of the microorganism or higher aquatic life form and the particular locus to be protected. Typically, the amount of the composition of the present invention to control the growth of microorganisms in a locus is sufficient if it provides from 0.1 to 1,000 ppm of the 3-isothiazoline ingredient of the composition in the locus. In one embodiment, the 3-isothiazolone ingredient of the composition is present in the locus in an amount of at least 0.5 ppm, in another embodiment at least 1 ppm, and in a further embodiment at least 10 ppm. In one embodiment, the isothiazolone ingredient of the composition is present in the locus in an amount of no more than 1000 ppm, in another embodiment no more than 500 ppm, and in a further embodiment no more than 200 ppm.

The compositions of this invention may optionally contain one or more additional microbicides in order to afford a composition having broader efficacy against microorganisms. Such microbicides are selected from known microbicides on the basis of their ability to control specific microorganisms and the specific locus to be preserved. Some embodiments of this invention comprise no additional microbicides.

EXAMPLES

Materials and Methods

The synergy of the combinations of the present invention was demonstrated by testing a wide range of concentrations and ratios of the compounds against the noted organisms. One skilled in the art will recognize that the sensitivity of other microorganisms to the particular combinations will vary and, as a result, the concentrations, the ratios, for each, or both, of the compounds may vary from those detailed in these examples. The concentrations and ratios may also vary under different test conditions or with different test methods.

One measure of synergy is the industrially accepted method described by Kull, F. C.; Eisman, P. C.; Sylwestrowicz, H. D. and Mayer, R. L., in *Applied Microbiology* 9:538-541 (1961), using the ratio determined by the formula:

$$Q_a/Q_A + Q_b/Q_B = \text{Synergy Index (``SI'')}$$

wherein:
$Q_A$=concentration of compound A (first component) in ppm, acting alone, which produced an end point (MIC of Compound A).
$Q_a$=concentration of compound A in ppm, in the mixture, which produced an end point.
$Q_B$=concentration of compound B (second component) in ppm, acting alone, which produced an end point (MIC of Compound B).
$Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergy is demonstrated. The lower the SI, the greater is the synergy shown by that particular mixture. The minimum inhibitory concentration (MIC) of a microbicide is the lowest concentration tested under a specific set of conditions that prevents the growth of the tested microorganisms.

Synergy tests were conducted using standard microtiter plate assays with media designed for optimal growth of the test microorganism. Minimal salt medium supplemented with 0.2% glucose and 0.1% yeast extract (M9GY medium) was used for testing bacteria; Potato Dextrose Broth (PDB medium) was used for testing yeast and mold. In this method, a wide range of combinations of microbicides and other personal care raw materials was tested by conducting high resolution MIC assays in the presence of various concentrations of MIT, or BIT. High resolution MICs were determined by adding varying amounts of microbicide to one column of a microtitre plate and doing subsequent ten-fold dilutions using an automated liquid handling system to obtain a series of endpoints ranging from 2 ppm to 10,000 ppm active ingredient.

The synergy of the combinations of the present invention was determined against a bacterium, *Escherichia coli* (*E. coli*—ATCC #8739), and/or a yeast, *Candida albicans* (*C. albicans*—ATCC 10231), and/or a mold, *Aspergillus niger* (*A. niger*—ATCC 16404). The bacteria were used at a concentration of about $5 \times 10^6$ bacteria per mL and the yeast and mold at $5 \times 10^5$ fungi per mL. These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the MIT combinations of the present invention are shown below in Tables 1 through 10. In each test, First Component (A) was MIT and the Second Component (B) was the other microbicide, formulation ingredient, or raw material. Each table shows the specific combinations of MIT and the second component; results against the microorganisms tested with incubation times; the end-point activity in ppm measured by the MIC for MIT alone ($Q_A$), for the second component alone ($Q_B$), for MIT in the mixture ($Q_a$) and for second component in the mixture ($Q_b$); the calculated SI value; and the range of synergistic ratios for each combination tested (MIT/second component or A/B) against the particular microorganism.

Similar test results for demonstration of synergy of the BIT combinations of the present invention are shown below in Tables 11 through 23.

In each of the comparisons, the effective synergistic ratio may vary among the microorganisms tested and the various combinations of components A and B. Data in the tables below include the range of ratios that were found to be synergistic. (Data which were collected outside of the synergistic ranges are not reported.) These data demonstrate that certain combinations of components A and B show enhanced control over the microorganisms than would be expected if the combinations were additive rather than synergistic.

TABLE 1

| Microorganism | $Q_a$ | $Q_b$ | SI |
|---|---|---|---|
| *A. niger* 16404—PDB | 0 | 2000 | 1.00 |
| (3 days) | 75 | 1000 | 0.75 |
|  | 100 | 1000 | 0.83 |
|  | 150 | 800 | 0.90 |
|  | 300 | 0 | 1.00 |

First Component (A) = Methylisothiazolinone (MIT)
Second Component (B) = anisic acid The ratios of MIT/anisic acid tested ranged from 1/0.05 to 1/1000. The synergistic ratios of MIT/anisic acid range from ca. 1/5 to ca. 1/13 when tested against mold.

TABLE 2

| Microorganism | $Q_a$ | $Q_b$ | SI |
|---|---|---|---|
| C. albicans 10231—PDB (2 days) | 0 | 2000 | 1.00 |
| | 20 | 1000 | 0.60 |
| | 40 | 1000 | 0.70 |
| | 60 | 1000 | 0.80 |
| | 80 | 80 | 0.44 |
| | 80 | 100 | 0.45 |
| | 80 | 200 | 0.50 |
| | 80 | 300 | 0.55 |
| | 80 | 400 | 0.60 |
| | 80 | 500 | 0.65 |
| | 80 | 600 | 0.70 |
| | 80 | 800 | 0.80 |
| | 80 | 1000 | 0.90 |
| | 100 | 80 | 0.54 |
| | 100 | 100 | 0.55 |
| | 100 | 200 | 0.60 |
| | 100 | 300 | 0.65 |
| | 100 | 400 | 0.70 |
| | 100 | 500 | 0.75 |
| | 100 | 600 | 0.80 |
| | 100 | 800 | 0.90 |
| | 150 | 400 | 0.95 |
| | 200 | 0 | 1.00 |
| A. niger 16404—PDB (3 days) | 0 | 2000 | 1.00 |
| | 100 | 400 | 0.70 |
| | 100 | 500 | 0.75 |
| | 100 | 600 | 0.80 |
| | 100 | 800 | 0.90 |
| | 150 | 200 | 0.85 |
| | 150 | 300 | 0.90 |
| | 150 | 400 | 0.95 |
| | 200 | 0 | 1.00 |

First Component (A) = Methylisothiazolinone (MIT)
Second Component (B) = decylene glycol The ratios of MIT/decylene glycol tested ranged from 1/0.05 to 1/1000. The synergistic ratios of MIT/decylene glycol range from 1/0.8 to 1/50 when tested against yeast and mold.

TABLE 3

| Microorganism | $Q_a$ | $Q_b$ | SI |
|---|---|---|---|
| C. albicans 10231—PDB (1 day) | 0 | 2000 | 1.00 |
| | 80 | 800 | 0.80 |
| | 80 | 1000 | 0.90 |
| | 100 | 600 | 0.80 |
| | 100 | 800 | 0.90 |
| | 200 | 0 | 1.00 |
| A. niger 16404—PDB (6 days) | 0 | 2000 | 1.00 |
| | 50 | 400 | 0.37 |
| | 50 | 500 | 0.42 |
| | 50 | 600 | 0.47 |
| | 50 | 800 | 0.57 |
| | 50 | 1000 | 0.67 |
| | 75 | 200 | 0.35 |
| | 75 | 300 | 0.40 |
| | 75 | 400 | 0.45 |
| | 75 | 500 | 0.50 |
| | 75 | 600 | 0.55 |
| | 75 | 800 | 0.65 |
| | 75 | 1000 | 0.75 |
| | 100 | 200 | 0.43 |
| | 100 | 300 | 0.48 |
| | 100 | 400 | 0.53 |
| | 100 | 500 | 0.58 |
| | 100 | 600 | 0.63 |
| | 100 | 800 | 0.73 |
| | 100 | 1000 | 0.83 |
| | 150 | 50 | 0.53 |
| | 150 | 60 | 0.53 |
| | 150 | 70 | 0.54 |
| | 150 | 80 | 0.54 |
| | 150 | 100 | 0.55 |
| | 150 | 200 | 0.60 |
| | 150 | 300 | 0.65 |
| | 150 | 400 | 0.70 |
| | 150 | 500 | 0.75 |
| | 150 | 600 | 0.80 |
| | 150 | 800 | 0.90 |
| | 200 | 10 | 0.67 |
| | 200 | 20 | 0.68 |
| | 200 | 30 | 0.68 |
| | 200 | 40 | 0.69 |
| | 200 | 50 | 0.69 |
| | 200 | 60 | 0.70 |
| | 200 | 80 | 0.71 |
| | 200 | 100 | 0.72 |
| | 200 | 200 | 0.77 |
| | 200 | 300 | 0.82 |
| | 200 | 400 | 0.87 |
| | 200 | 500 | 0.92 |
| | 200 | 600 | 0.97 |
| | 300 | 0 | 1.00 |

First Component (A) = Methylisothiazolinone (MIT)
Second Component (B) = diethylene triamine pentacetic acid (DTPA)

The ratios of MIT/DTPA tested ranged from 1/0.05 to 1/1000. The synergistic ratios of MIT/DTPA range from 1/0.05 to 1/20 when tested against yeast and mold.

TABLE 4

| Microorganism | $Q_a$ | $Q_b$ | SI |
|---|---|---|---|
| C. albicans 10231—PDB (1 day) | 0 | 2000 | 1.00 |
| | 80 | 600 | 0.70 |
| | 80 | 800 | 0.80 |
| | 80 | 1000 | 0.90 |
| | 100 | 100 | 0.55 |
| | 100 | 200 | 0.60 |
| | 100 | 300 | 0.65 |
| | 100 | 400 | 0.70 |
| | 100 | 500 | 0.75 |
| | 100 | 600 | 0.80 |
| | 100 | 800 | 0.90 |
| | 200 | 0 | 1.00 |
| A. niger 16404—PDB (3 days) | 0 | 10000 | 1.00 |
| | 50 | 4000 | 0.57 |
| | 50 | 5000 | 0.67 |
| | 50 | 6000 | 0.77 |
| | 50 | 8000 | 0.97 |
| | 75 | 2000 | 0.45 |
| | 75 | 3000 | 0.55 |
| | 75 | 4000 | 0.65 |
| | 75 | 5000 | 0.75 |
| | 75 | 6000 | 0.85 |
| | 100 | 400 | 0.37 |
| | 100 | 500 | 0.38 |
| | 100 | 600 | 0.39 |
| | 100 | 800 | 0.41 |
| | 100 | 1000 | 0.43 |
| | 100 | 2000 | 0.53 |
| | 100 | 3000 | 0.63 |
| | 100 | 4000 | 0.73 |
| | 100 | 5000 | 0.83 |
| | 100 | 6000 | 0.93 |
| | 150 | 50 | 0.51 |
| | 150 | 60 | 0.51 |
| | 150 | 80 | 0.51 |
| | 150 | 100 | 0.51 |
| | 150 | 200 | 0.52 |
| | 150 | 300 | 0.53 |
| | 150 | 400 | 0.54 |
| | 150 | 500 | 0.55 |
| | 150 | 600 | 0.56 |
| | 150 | 800 | 0.58 |
| | 150 | 1000 | 0.60 |
| | 150 | 2000 | 0.70 |
| | 150 | 3000 | 0.80 |
| | 150 | 4000 | 0.90 |
| | 200 | 10 | 0.67 |

TABLE 4-continued

| Microorganism | $Q_a$ | $Q_b$ | SI |
|---|---|---|---|
| | 200 | 20 | 0.67 |
| | 200 | 30 | 0.67 |
| | 200 | 40 | 0.67 |
| | 200 | 50 | 0.67 |
| | 200 | 60 | 0.67 |
| | 200 | 80 | 0.67 |
| | 200 | 100 | 0.68 |
| | 200 | 200 | 0.69 |
| | 200 | 300 | 0.70 |
| | 200 | 400 | 0.71 |
| | 200 | 500 | 0.72 |
| | 200 | 600 | 0.73 |
| | 200 | 800 | 0.75 |
| | 200 | 1000 | 0.77 |
| | 200 | 2000 | 0.87 |
| | 200 | 3000 | 0.97 |
| | 300 | 0 | 1.00 |

First Component (A) = Methylisothiazolinone (MIT)
Second Component (B) = hydroxyethyl ethylenediamine triacetic acid (HEDTA)

The ratios of MIT/HEDTA tested ranged from 1/0.05 to 1/1000. The synergistic ratios of MIT/HEDTA range from 1/0.05 to 1/160 when tested against yeast and mold.

TABLE 5

| Microorganism | $Q_a$ | $Q_b$ | SI |
|---|---|---|---|
| C. albicans 10231—PDB | 0 | 8000 | 1.00 |
| (2 days) | 20 | 6000 | 0.85 |
| | 40 | 5000 | 0.83 |
| | 40 | 6000 | 0.95 |
| | 60 | 4000 | 0.80 |
| | 60 | 5000 | 0.93 |
| | 80 | 2000 | 0.65 |
| | 80 | 3000 | 0.78 |
| | 80 | 4000 | 0.90 |
| | 100 | 800 | 0.60 |
| | 100 | 1000 | 0.63 |
| | 100 | 2000 | 0.75 |
| | 100 | 3000 | 0.88 |
| | 200 | 0 | 1.00 |
| A. niger 16404—PDB | 0 | 5000 | 1.00 |
| (3 days) | 100 | 2000 | 0.73 |
| | 100 | 3000 | 0.93 |
| | 150 | 2000 | 0.90 |
| | 200 | 400 | 0.75 |
| | 200 | 500 | 0.77 |
| | 200 | 600 | 0.79 |
| | 200 | 800 | 0.83 |
| | 200 | 1000 | 0.87 |
| | 300 | 0 | 1.00 |

First Component (A) = Methylisothiazolinone (MIT)
Second Component (B) = iminodisuccinate (IDS)

The ratios of MIT/IDS tested ranged from 1/0.05 to 1/1000. The synergistic ratios of MIT/IDS range from 1/2 to 1/300 when tested against yeast and mold.

TABLE 6

| Microorganism | $Q_a$ | $Q_b$ | SI |
|---|---|---|---|
| C. albicans 10231—PDB | 0 | 4000 | 1.00 |
| (2 days) | 10 | 3000 | 0.80 |
| | 20 | 3000 | 0.85 |
| | 25 | 3000 | 0.88 |
| | 30 | 3000 | 0.90 |
| | 40 | 2000 | 0.70 |
| | 40 | 3000 | 0.95 |
| | 200 | 0 | 1.00 |

First Component (A) = Methylisothiazolinone (MIT)
Second Component (B) = maleic acid The ratios of MIT/maleic acid tested ranged from 1/0.05 to 1/1000. The synergistic ratios of MIT/maleic acid range from 1/50 to 1/300 when tested against yeast.

TABLE 7

| Microorganism | $Q_a$ | $Q_b$ | SI |
|---|---|---|---|
| C. albicans 10231—PDB | 0 | 20000 | 1.00 |
| (3 days) | 40 | 8000 | 0.60 |
| | 40 | 10000 | 0.70 |
| | 60 | 6000 | 0.60 |
| | 60 | 8000 | 0.70 |
| | 60 | 10000 | 0.80 |
| | 80 | 4000 | 0.60 |
| | 80 | 5000 | 0.65 |
| | 80 | 6000 | 0.70 |
| | 80 | 8000 | 0.80 |
| | 80 | 10000 | 0.90 |
| | 100 | 3000 | 0.65 |
| | 100 | 4000 | 0.70 |
| | 100 | 5000 | 0.75 |
| | 100 | 6000 | 0.80 |
| | 100 | 8000 | 0.90 |
| | 200 | 0 | 1.00 |
| A. niger 16404—PDB | 0 | 20000 | 1.00 |
| (10 days) | 75 | 8000 | 0.65 |
| | 75 | 10000 | 0.75 |
| | 150 | 4000 | 0.70 |
| | 150 | 6000 | 0.80 |
| | 150 | 8000 | 0.90 |
| | 200 | 3000 | 0.82 |
| | 200 | 4000 | 0.87 |
| | 200 | 5000 | 0.92 |
| | 200 | 6000 | 0.97 |
| | 300 | 0 | 1.00 |

First Component (A) = Methylisothiazolinone (MIT)
Second Component (B) = methyl glycine diacetic acid (MDGA)

The ratios of MIT/MDGA tested ranged from 1/0.05 to 1/1000. The synergistic ratios of MIT/MDGA range from 1/15 to 1/250 when tested against yeast and mold.

TABLE 8

| Microorganism | $Q_a$ | $Q_b$ | SI |
|---|---|---|---|
| C. albicans 10231—PDB | 0 | 5000 | 1.00 |
| (3 days) | 20 | 4000 | 0.90 |
| | 40 | 3000 | 0.80 |
| | 40 | 3000 | 0.80 |
| | 60 | 2000 | 0.70 |
| | 60 | 2000 | 0.70 |
| | 60 | 3000 | 0.90 |
| | 80 | 600 | 0.52 |
| | 80 | 800 | 0.56 |
| | 80 | 1000 | 0.60 |
| | 80 | 2000 | 0.80 |
| | 100 | 400 | 0.58 |
| | 100 | 500 | 0.60 |
| | 100 | 600 | 0.62 |
| | 100 | 800 | 0.66 |
| | 100 | 1000 | 0.70 |
| | 100 | 2000 | 0.90 |
| | 200 | 0 | 1.00 |

First Component (A) = Methylisothiazolinone (MIT)
Second Component (B) = phenoxypropanol The ratios of MIT/phenoxypropanol tested ranged from 1/0.05 to 1/1000. The synergistic ratios of MIT/phenoxypropanol range from 1/4 to 1/200 when tested against yeast.

TABLE 9

| Microorganism | $Q_a$ | $Q_b$ | SI |
|---|---|---|---|
| A. niger 16404—PDB | 0 | 20000 | 1.00 |
| (10 days) | 100 | 10000 | 0.83 |
|  | 150 | 4000 | 0.70 |
|  | 150 | 5000 | 0.75 |
|  | 150 | 6000 | 0.80 |
|  | 150 | 8000 | 0.90 |
|  | 200 | 2000 | 0.77 |
|  | 200 | 3000 | 0.82 |
|  | 200 | 4000 | 0.87 |
|  | 200 | 5000 | 0.92 |
|  | 200 | 6000 | 0.97 |
|  | 300 | 0 | 1.00 |

First Component (A) = Methylisothiazolinone (MIT)
Second Component (B) = phytic acid The ratios of MIT/phytic acid tested ranged from 1/0.05 to 1/1000. The synergistic ratios of MIT/phytic acid range from 1/10 to 1/100 when tested against mold.

TABLE 10

| Microorganism | $Q_a$ | $Q_b$ | SI |
|---|---|---|---|
| C. albicans 10231—PDB | 0 | 2000 | 1.00 |
| (2 days) | 40 | 1000 | 0.70 |
|  | 60 | 800 | 0.70 |
|  | 60 | 1000 | 0.80 |
|  | 80 | 600 | 0.70 |
|  | 80 | 800 | 0.80 |
|  | 80 | 1000 | 0.90 |
|  | 200 | 0 | 1.00 |

First Component (A) = Methylisothiazolinone (MIT)
Second Component (B) = propionic acid The ratios of MIT/propionic acid tested ranged from 1/0.05 to 1/1000. The synergistic ratios of MIT/propionic acid range from 1/7.5 to 1/25 when tested against yeast.

TABLE 11

| Microorganism | $Q_a$ | $Q_b$ | SI |
|---|---|---|---|
| E. coli 8739—M9GY | 0 | 8000 | 1.00 |
| (1 day) | 10 | 300 | 0.70 |
|  | 10 | 400 | 0.72 |
|  | 10 | 500 | 0.73 |
|  | 10 | 600 | 0.74 |
|  | 10 | 800 | 0.77 |
|  | 10 | 1000 | 0.79 |
|  | 10 | 2000 | 0.92 |
|  | 15 | 0 | 1.00 |
| A. niger 16404—PDB | 0 | 2000 | 1.00 |
| (3 days) | 5 | 1000 | 0.75 |
|  | 7.5 | 800 | 0.78 |
|  | 7.5 | 1000 | 0.88 |
|  | 10 | 800 | 0.90 |
|  | 20 | 0 | 1.00 |

First Component (A) = Benzisothiazolinone (BIT)
Second Component (B) = anisic acid The ratios of BIT/anisic acid tested ranged from 1/0.05 to 1/1000. The synergistic ratios of BIT/anisic acid range from 1/30 to 1/1000 when tested against bacteria and mold.

TABLE 12

| Microorganism | $Q_a$ | $Q_b$ | SI |
|---|---|---|---|
| E. coli 8739—M9GY | 0 | 10000 | 1.00 |
| (3 days) | 10 | 2000 | 0.87 |
|  | 10 | 3000 | 0.97 |
|  | 15 | 0 | 1.00 |
| C. albicans 10231—PDB | 0 | 2000 | 1.00 |
| (2 days) | 20 | 600 | 0.80 |
|  | 20 | 800 | 0.90 |
|  | 40 | 0 | 1.00 |
| A. niger 16404—PDB | 0 | 5000 | 1.00 |
| (6 days) | 5 | 2000 | 0.65 |
|  | 5 | 3000 | 0.85 |
|  | 10 | 2000 | 0.90 |
|  | 20 | 0 | 1.00 |

First Component (A) = Benzisothiazolinone (BIT)
Second Component (B) = capric acid The ratios of BIT/capric acid tested ranged from 1/0.05 to 1/1000. The synergistic ratios of BIT/capric acid range from 1/30 to 1/600 when tested against bacteria, yeast, and mold.

TABLE 13

| Microorganism | $Q_a$ | $Q_b$ | SI |
|---|---|---|---|
| C. albicans 10231—PDB | 0 | 2000 | 1.00 |
| (1 day) | 7.5 | 800 | 0.78 |
|  | 7.5 | 1000 | 0.88 |
|  | 10 | 500 | 0.75 |
|  | 10 | 600 | 0.80 |
|  | 10 | 800 | 0.90 |
|  | 20 | 0 | 1.00 |

First Component (A) = Benzisothiazolinone (BIT)
Second Component (B) = decylene glycol The ratios of BIT/decylene glycol tested ranged from 1/0.05 to 1/1000. The synergistic ratios of BIT/decylene glycol range from 1/50 to 1/133 when tested against yeast.

TABLE 14

| Microorganism | $Q_a$ | $Q_b$ | SI |
|---|---|---|---|
| A. niger 16404—PDB | 0 | 800 | 1.00 |
| (3 days) | 5 | 200 | 0.50 |
|  | 5 | 300 | 0.63 |
|  | 5 | 400 | 0.75 |
|  | 5 | 500 | 0.88 |
|  | 8 | 200 | 0.63 |
|  | 7.5 | 300 | 0.75 |
|  | 7.5 | 400 | 0.88 |
|  | 10 | 40 | 0.55 |
|  | 10 | 50 | 0.56 |
|  | 10 | 60 | 0.58 |
|  | 10 | 80 | 0.60 |
|  | 10 | 100 | 0.63 |
|  | 10 | 200 | 0.75 |
|  | 10 | 300 | 0.88 |
|  | 15 | 10 | 0.76 |
|  | 15 | 20 | 0.78 |
|  | 15 | 30 | 0.79 |
|  | 15 | 40 | 0.80 |
|  | 15 | 50 | 0.81 |
|  | 15 | 60 | 0.83 |
|  | 15 | 80 | 0.85 |
|  | 10 | 100 | 0.63 |
|  | 10 | 200 | 0.75 |
|  | 10 | 300 | 0.88 |
|  | 15 | 10 | 0.76 |
|  | 15 | 20 | 0.78 |
|  | 15 | 30 | 0.79 |
|  | 15 | 40 | 0.80 |
|  | 15 | 50 | 0.81 |
|  | 15 | 60 | 0.83 |
|  | 15 | 80 | 0.85 |

TABLE 14-continued

| Microorganism | $Q_a$ | $Q_b$ | SI |
|---|---|---|---|
| | 15 | 100 | 0.88 |
| | 20 | 0 | 1.00 |

First Component (A) = Benzisothiazolinone (BIT)
Second Component (B) = diethylene triamine pentacetic acid (DTPA)

The ratios of BIT/DTPA tested ranged from 1/0.05 to 1/1000. The synergistic ratios of BIT/DTPA range from 1/0.7 to 1/100 when tested against mold.

TABLE 15

| Microorganism | $Q_a$ | $Q_b$ | SI |
|---|---|---|---|
| A. niger 16404—PDB | 0 | 2000 | 1.00 |
| (10 days) | 5 | 1000 | 0.75 |
| | 7.5 | 1000 | 0.88 |
| | 10 | 800 | 0.90 |
| | 15 | 400 | 0.95 |
| | 20 | 0 | 1.00 |

First Component (A) = Benzisothiazolinone (BIT)
Second Component (B) = etidronic acid The ratios of BIT/etidronic acid tested ranged from 1/0.05 to 1/1000. The synergistic ratios of BIT/etidronic acid range from 1/27 to 1/200 when tested against mold.

TABLE 16

| Microorganism | $Q_a$ | $Q_b$ | SI |
|---|---|---|---|
| E. coli 8739—M9GY | 0 | 20000 | 1.00 |
| (2 days) | 10 | 800 | 0.71 |
| | 10 | 1000 | 0.72 |
| | 10 | 2000 | 0.77 |
| | 10 | 3000 | 0.82 |
| | 10 | 4000 | 0.87 |
| | 10 | 5000 | 0.92 |
| | 10 | 6000 | 0.97 |
| | 15 | 0 | 1.00 |

First Component (A) = Benzisothiazolinone (BIT)
Second Component (B) = gluconic acid The ratios of BIT/gluconic acid tested ranged from 1/0.05 to 1/1000. The synergistic ratios of BIT/gluconic acid range from 1/80 to 1/600 when tested against bacteria.

TABLE 17

| Microorganism | $Q_a$ | $Q_b$ | SI |
|---|---|---|---|
| E. coli 8739—M9GY | 0 | 20000 | 1.00 |
| (1 day) | 10 | 1000 | 0.72 |
| | 10 | 2000 | 0.77 |
| | 10 | 3000 | 0.82 |
| | 10 | 4000 | 0.87 |
| | 10 | 5000 | 0.92 |
| | 10 | 6000 | 0.97 |
| | 15 | 0 | 1.00 |
| A. niger 16404—PDB | 0 | 10000 | 1.00 |
| (3 days) | 5 | 5000 | 0.75 |
| | 5 | 6000 | 0.85 |
| | 7.5 | 3000 | 0.68 |
| | 7.5 | 4000 | 0.78 |
| | 7.5 | 5000 | 0.88 |
| | 7.5 | 6000 | 0.98 |
| | 10 | 800 | 0.58 |
| | 10 | 1000 | 0.60 |
| | 10 | 2000 | 0.70 |
| | 10 | 3000 | 0.80 |
| | 10 | 4000 | 0.90 |
| | 15 | 200 | 0.77 |
| | 15 | 300 | 0.78 |

TABLE 17-continued

| Microorganism | $Q_a$ | $Q_b$ | SI |
|---|---|---|---|
| | 15 | 400 | 0.79 |
| | 15 | 500 | 0.80 |
| | 15 | 600 | 0.81 |
| | 15 | 800 | 0.83 |
| | 15 | 1000 | 0.85 |
| | 15 | 2000 | 0.95 |
| | 300 | 0 | 1.00 |

First Component (A) = Benzisothiazolinone (BIT)
Second Component (B) = hydroxyethyl ethylenediamine triacetic acid (HEDTA)

The ratios of BIT/HEDTA tested ranged from 1/0.05 to 1/1000. The synergistic ratios of BIT/HEDTA range from 1/13 to 1/1200 when tested against bacteria and mold.

TABLE 18

| Microorganism | $Q_a$ | $Q_b$ | SI |
|---|---|---|---|
| C. albicans 10231—PDB | 0 | 20000 | 1.00 |
| (2 days) | 7.5 | 10000 | 0.88 |
| | 10 | 8000 | 0.90 |
| | 200 | 0 | 1.00 |

First Component (A) = Benzisothiazolinone (BIT)
Second Component (B) = iminodisuccinate (IDS)

The ratios of BIT/IDS tested ranged from 1/0.05 to 1/1000. The synergistic ratios of BIT/IDS range from 1/800 to 1/1300 when tested against yeast.

TABLE 19

| Microorganism | $Q_a$ | $Q_b$ | SI |
|---|---|---|---|
| E. coli 8739—M9GY | 0 | 8000 | 1.00 |
| (1 day) | 10 | 300 | 0.70 |
| | 10 | 400 | 0.72 |
| | 10 | 500 | 0.73 |
| | 10 | 600 | 0.74 |
| | 10 | 800 | 0.77 |
| | 10 | 1000 | 0.79 |
| | 10 | 2000 | 0.92 |
| | 15 | 0 | 1.00 |
| C. albicans 10231—PDB | 0 | 20000 | 1.00 |
| (2 days) | 10 | 10000 | 0.75 |
| | 20 | 8000 | 0.90 |
| | 40 | 0 | 1.00 |

First Component (A) = Benzisothiazolinone (BIT)
Second Component (B) = maleic acid The ratios of BIT/maleic acid tested ranged from 1/0.05 to 1/1000. The synergistic ratios of BIT/maleic acid range from 1/30 to 1/1000 when tested against bacteria and yeast.

TABLE 20

| Microorganism | $Q_a$ | $Q_b$ | SI |
|---|---|---|---|
| C. albicans 10231—PDB | 0 | 5000 | 1.00 |
| (3 days) | 2.5 | 4000 | 0.86 |
| | 5 | 4000 | 0.93 |
| | 7.5 | 3000 | 0.79 |
| | 10 | 2000 | 0.65 |
| | 10 | 3000 | 0.85 |
| | 20 | 400 | 0.58 |
| | 20 | 500 | 0.60 |
| | 20 | 600 | 0.62 |
| | 20 | 800 | 0.66 |
| | 20 | 1000 | 0.70 |
| | 20 | 2000 | 0.90 |
| | 40 | 0 | 1.00 |

TABLE 20-continued

| Microorganism | $Q_a$ | $Q_b$ | SI |
|---|---|---|---|
| A. niger 16404—PDB (10 days) | 0 | 3000 | 1.00 |
| | 5 | 1000 | 0.58 |
| | 5 | 2000 | 0.92 |
| | 7.5 | 800 | 0.64 |
| | 7.5 | 1000 | 0.71 |
| | 10 | 800 | 0.77 |
| | 10 | 1000 | 0.83 |
| | 15 | 600 | 0.95 |
| | 20 | 0 | 1.00 |

First Component (A) = Benzisothiazolinone (BIT)
Second Component (B) = methyl glycine diacetic acid (MDGA The ratios of BIT/MDGA tested ranged from 1/0.05 to 1/1000. The synergistic ratios of BIT/MDGA range from 1/20 to 1/1600 when tested against yeast and mold.

TABLE 21

| Microorganism | $Q_a$ | $Q_b$ | SI |
|---|---|---|---|
| C. albicans 10231—PDB (3 days) | 0 | 5000 | 1.00 |
| | 2.5 | 4000 | 0.86 |
| | 5 | 4000 | 0.93 |
| | 7.5 | 3000 | 0.79 |
| | 10 | 2000 | 0.65 |
| | 10 | 3000 | 0.85 |
| | 20 | 400 | 0.58 |
| | 20 | 500 | 0.60 |
| | 20 | 600 | 0.62 |
| | 20 | 800 | 0.66 |
| | 20 | 1000 | 0.70 |
| | 20 | 2000 | 0.90 |
| | 200 | 0 | 1.00 |
| A. niger 16404—PDB (3 days) | 0 | 3000 | 1.00 |
| | 5 | 1000 | 0.58 |
| | 5 | 2000 | 0.92 |
| | 7.5 | 800 | 0.64 |
| | 7.5 | 1000 | 0.71 |
| | 10 | 800 | 0.77 |
| | 10 | 1000 | 0.83 |
| | 15 | 600 | 0.95 |
| | 20 | 0 | 1.00 |

First Component (A) = Benzisothiazolinone (BIT)
Second Component (B) = phenoxypropanol The ratios of BIT/phenoxypropanol tested ranged from 1/0.05 to 1/1000. The synergistic ratios of BIT/phenoxypropanol range from 1/20 to 1/1600 when tested against yeast and mold.

TABLE 22

| Microorganism | $Q_a$ | $Q_b$ | SI |
|---|---|---|---|
| E. coli 8739—M9GY (1 day) | 0 | 5000 | 1.00 |
| | 10 | 60 | 0.68 |
| | 10 | 80 | 0.68 |
| | 10 | 100 | 0.69 |
| | 10 | 200 | 0.71 |
| | 10 | 300 | 0.73 |
| | 10 | 400 | 0.75 |
| | 10 | 500 | 0.77 |
| | 10 | 600 | 0.79 |
| | 10 | 800 | 0.83 |
| | 10 | 1000 | 0.87 |
| | 15 | 0 | 1.00 |
| C. albicans 10231—PDB (2 days) | 0 | 3000 | 1.00 |
| | 10 | 2000 | 0.92 |
| | 40 | 0 | 1.00 |
| A. niger 16404—PDB (10 days) | 0 | 20000 | 1.00 |
| | 7.5 | 10000 | 0.88 |
| | 10 | 8000 | 0.90 |
| | 15 | 2000 | 0.85 |

TABLE 22-continued

| Microorganism | $Q_a$ | $Q_b$ | SI |
|---|---|---|---|
| | 15 | 3000 | 0.90 |
| | 15 | 4000 | 0.95 |
| | 20 | 0 | 1.00 |

First Component (A) = Benzisothiazolinone (BIT)
Second Component (B) = phytic acid The ratios of BIT/phytic acid tested ranged from 1/0.05 to 1/1000. The synergistic ratios of BIT/phytic acid range from 1/6 to 1/1300 when tested against bacteria, yeast, and mold.

TABLE 23

| Microorganism | $Q_a$ | $Q_b$ | SI |
|---|---|---|---|
| E. coli 8739—M9GY (1 day) | 0 | 5000 | 1.00 |
| | 10 | 60 | 0.68 |
| | 10 | 80 | 0.68 |
| | 10 | 100 | 0.69 |
| | 10 | 200 | 0.71 |
| | 15 | 0 | 1.00 |
| C. albicans 10231—PDB (1 day) | 0 | 2000 | 1.00 |
| | 1 | 1000 | 0.55 |
| | 2.5 | 1000 | 0.63 |
| | 5 | 1000 | 0.75 |
| | 7.5 | 800 | 0.78 |
| | 7.5 | 1000 | 0.88 |
| | 10 | 800 | 0.90 |
| | 20 | 0 | 1.00 |
| A. niger 16404—PDB (10 days) | 0 | 500 | 1.00 |
| | 15 | 30 | 0.81 |
| | 15 | 40 | 0.83 |
| | 15 | 50 | 0.85 |
| | 15 | 60 | 0.87 |
| | 15 | 80 | 0.91 |
| | 15 | 100 | 0.95 |
| | 20 | 0 | 1.00 |

First Component (A) = Benzisothiazolinone (BIT)
Second Component (B) = propionic acid The ratios of BIT/propionic acid tested ranged from 1/0.05 to 1/1000. The synergistic ratios of BIT/propionic acid range from 1/2 to 1/1000 when tested against bacteria, yeast, and mold.

Using test methods similar to those described above, no synergy was found in comparative combinations of MIT with capric acid, calcium gluconate, etidronic acid, gluconic acid, lactobionic acid, lauric acid, magnesium citrate, or succinic acid. No synergy was found in combinations of BIT with calcium gluconate, lactobionic acid, lauric acid, magnesium citrate, or succinic acid. These results support the unexpected synergy in the claimed compositions.

Furthermore, in earlier studies, MIT was tested in combination with other biocides against various organisms, including P. aeruginosa, C. albicans, S. aureus, A. niger and E. coli. The results showed that there was no synergistic interaction against at least some of the organisms tested for MIT combinations with benzoic acid, benzyl alcohol, butylene glycol, citric acid, DMDMH, EDDS, IPBC, hexylene glycol, pentylene glycol, propylparaben, sorbic acid, DBDCB or zinc pyrithione. In addition, other earlier synergy studies were conducted with MIT in combination with a range of commercial biocides, which ultimately led to combinations claimed in U.S. Pat. No. 5,489,588. Under the conditions of those studies, conducted against E. coli and C. albicans, seven MIT combinations were found to be synergistic: p-chloro-m-xylenol, sodium dichlorophene, bis-(2-hydroxy-5-chlorophenyl)sulfide, benzylbromoacetate, dodecylamine, 4-(2-nitrobutyl)morpholine, and dipropylamine ether. However, twenty-nine additional combinations with MIT were tested and were not synergistic against these two microbes: 4,4-dimethyloxazolidine, 2-(hydroxymethyl)-2-nitro-1,3-propanediol, N-methylolchloroacetamide, 2,2-dibromo-3-nitrilopropionamide (however, in subsequent testing using different microbes and test conditions, this combination was found to be synergistic), bromonitrostyrene, glutaraldehyde, 2-(hydroxymethyl)aminoethanol, 2-(hydroxymethyl)amino-2-methylpropanol, poly[oxy-ethylenedimethyliminoethylene dimethyliminoethylene)chloride], benzoylchloroformaldoxime, 1,2-dibromo-2,4-dicyanobutane, 2-thiocyanomethylthiobendazole, N,N'-dihydroxymethyl-5,5-dimethyl hydantoin, hexahydro-1,3,5-(2-hydroxyethyl)triazine, hexahydro-1,3,5-triethyl-s-triazine, bis-(trichloromethyl)sulfone, blend of bis-(tributyltin)oxide/2-(hydroxymethyl)aminoethanol, bis-(tributyltin)oxide, imidazolidinyl urea, diazolidinyl urea, N,N-dimethyl-N'-phenyl-N'-(fluorodichloromethylthio)sulfamide, c is 1-(3-chloroallyl)-3,5,7-triaza-1-azoniaadamantane chloride, diiodomethyl-p-tolylsulfone, 2,4-dichlorobenzylalcohol, didodecyldimethylammonium chloride, methylene-b-thiocyanate, 2-bromo-2-nitropropane-1,3-diol, bis-(2-hydroxy-5-chlorophenyl)sulfide, 5-bromo-5-nitro-1,3-dioxane, and 3-iodo-2-propynylbutylcarbamate. One skilled in the art of biocide development and testing would have been aware of similar results from testing other biocide combinations and would not have expected that any particular combination of biocides could be predicted to exhibit a synergistic interaction.

We claim:

1. A composition comprising a microbicidally synergistic mixture of:
   (a) 2-methyl-4-isothiazolin-3-one; and
   (b) one or more compounds selected from the group consisting of anisic acid, decylene glycol, diethylene triamine pentacetic acid (DTPA), hydroxyethyl ethylenediamine triacetic acid (HEDTA), imminodisuccinate (IDS), maleic acid, methyl glycine diacetic acid (MDGA), phenoxypropanol, phytic acid, and propionic acid.

2. A composition comprising a microbicidally synergistic mixture of:
   (a) 1,2-benzisothiazolin-3-one; and
   (b) one or more compounds selected from the group consisting of anisic acid, capric acid, decylene glycol, diethylene triamine pentacetic acid (DTPA), etidronic acid, gluconic acid, hydroxyethyl ethylenediamine triacetic acid (HEDTA), imminodisuccinate (IDS), maleic acid, methyl glycine diacetic acid (MDGA), phenoxypropanol, phytic acid, and propionic acid.

* * * * *

UNITED STATES PATENT AND TRADEMARK OFFICE
CERTIFICATE OF CORRECTION

PATENT NO. : 8,138,212 B2
APPLICATION NO. : 12/842122
DATED : March 20, 2012
INVENTOR(S) : Megan Ann Diehl and Dolores Ann Shaw It is certified that error appears in the above-identified patent and that said Letters Patent is hereby corrected as shown below:

IN THE SPECIFICATIONS:

Column 14, Table 17 (BIT/HECTA), the last line (8) of the table, please replace "300  0  1.00" with "20  0  1.00"

Column 14, Table 18 (BIT/IDS), the last line (5) of the table, please replace "200  0  1.00" with "20  0  1.00"

Column 15, Table 21 (BIT/phenoxypropanol), line 13 of the table, please replace "200  0  1.00" with "40  0  1.00"

Signed and Sealed this
Fourth Day of September, 2012

David J. Kappos
*Director of the United States Patent and Trademark Office*